(12) United States Patent
Strässler et al.

(10) Patent No.: US 7,789,829 B2
(45) Date of Patent: Sep. 7, 2010

(54) SENSOR SYSTEM FOR DETERMINING THE CONCENTRATION OF GLUCOSE IN BLOOD

(75) Inventors: Sigfrid Strässler, St-Saphorin-s-Morges (CH); Peter Ryser, Morges (CH); Klaus Ganz, Küsnacht (CH); Jacques Jacot, Fontaines (CH)

(73) Assignee: Ecole Polytechnique Federale de Lausanne, Lausanne (CH)

( * ) Notice: Subject to any disclaimer, the term of this patent is extended or adjusted under 35 U.S.C. 154(b) by 1447 days.

(21) Appl. No.: 10/532,897

(22) PCT Filed: Oct. 22, 2003

(86) PCT No.: PCT/CH03/00684

§ 371 (c)(1),
(2), (4) Date: Apr. 27, 2005

(87) PCT Pub. No.: WO2004/037079

PCT Pub. Date: May 6, 2004

(65) Prior Publication Data

US 2006/0100493 A1    May 11, 2006

(30) Foreign Application Priority Data

Oct. 28, 2002    (EP) .................................. 02024022
May 16, 2003    (CH) ..................................... 0887/03

(51) Int. Cl.
*A61B 5/00* (2006.01)
(52) U.S. Cl. ...................................... 600/365; 73/54.01
(58) Field of Classification Search .................. 600/309, 600/365; 73/54.01–54.43
See application file for complete search history.

(56) References Cited

U.S. PATENT DOCUMENTS

| 5,494,639 | A | 2/1996 | Grzegorzewski |
| 5,547,049 | A * | 8/1996 | Weiss et al. ............... 188/267.2 |
| 6,200,532 | B1 * | 3/2001 | Wu et al. ....................... 422/73 |
| 6,201,980 | B1 | 3/2001 | Darrow et al. |
| 6,210,326 | B1 | 4/2001 | Ehwald |
| 6,267,002 | B1 * | 7/2001 | Ehwald et al. ............. 73/54.01 |
| 6,271,044 | B1 | 8/2001 | Ballerstadt et al. |
| 7,226,414 | B2 * | 6/2007 | Ballerstadt et al. .......... 600/365 |
| 2001/0045122 | A1 | 11/2001 | Ehwald et al. |
| 2003/0230136 | A1 * | 12/2003 | Wright ...................... 73/54.25 |

* cited by examiner

*Primary Examiner*—Patricia C Mallari
*Assistant Examiner*—Karen E Toth
(74) *Attorney, Agent, or Firm*—Clifford W. Browning; Krieg DeVault LLP

(57) ABSTRACT

The sensor system comprises an implantable sensor and a user device associated with it. A sensitive liquid is enclosed in the sensor, into which glucose can penetrate. The viscosity of the mixture of sensitive liquid and glucose is measured. The user device, which controls the measurement and its evaluation, is a portable device worn externally on the skin. The viscosity is measured based on the rotation of a measuring element driven by a driving magnet, both disposed in the sensor. The rotation of the measuring element is analyzed based on its decay behavior following switch-off of the driving magnet. In a second embodiment, the viscosity is measured based on the oscillatory behavior of an oscillating element excited to oscillate by a magnet, both disposed in the sensor. The oscillatory behavior is analyzed based on the decay behavior of the oscillating element following switch-off of the magnet.

21 Claims, 3 Drawing Sheets

SENSOR SYSTEM FOR DETERMINING THE CONCENTRATION OF GLUCOSE IN BLOOD

Applicants claim foreign priority benefits under 35 U.S.C. §§119(a)-(d) or (f), or §365(b) of European Patent Application No. EP 02 024 022.2, filed Oct. 28, 2002; and of Swiss Patent Application No. 0887/03, filed May 16, 2003.

The subject-matter of the invention is the measurement of blood sugar by means of an implantable sensor. Diabetes mellitus (diabetes) is one of the most common chronic illnesses. It affects about 8% of the US population and, due to increasing overweight in the population, this figure is increasing annually. It is expected that, worldwide, there will be about 300 million diabetics by the year 2025. If diabetes is inadequately treated over many years, there is a high risk of heart attack, stroke, blood circulation disorders in the lower extremities, kidney damage and blindness, as well as nerve conduction disorders, which can result in foot or leg amputations. Diabetes thus accounts for about 10% of all health service costs.

Through various studies, such as the Diabetes Control and Complication Trial (DCCT) and the UK Prospective Diabetes Study (UKPDS), it has been possible to demonstrate that the risk of long-term complications can be reduced through improved adjustment of blood sugar. Various types of treatment are available for reducing blood sugar: an adapted diet, physical activity, tablets and insulin. An essential element in checking the efficacy of the respective treatment is that of self-monitoring of blood sugar. All insulin-dependent diabetics (Type 1) and certain non-insulin-dependent diabetics (Type 2) should measure their blood sugar several times per day. Hitherto, this has been performed by pricking the tip of a finger and applying a small quantity of blood to a test strip, which is inserted in a reading device. This method of self-monitoring is both painful and costly. For years, therefore, it has been sought to develop a painless method for continuous measurement of blood sugar. As many blood-sugar measurements as possible should enable the doctors and patients routinely to adapt and improve the treatments, as a result of which the risk of long-term complications and the consequent costs can be reduced.

The present invention relates to a sensor system for determining the glucose concentration in blood, comprising an implantable sensor and a user device associated with the latter.

Known in the art is a transcutaneous system with an implantable sensor having a needle which comprises two different metals that are separated by an insulator, so that an electric potential can be applied. The sensor is connected to a monitor which records the glucose values every 5 minutes over a maximum of 3 days. The sensor is not very stable, with the result that it is necessary for a calibration to be performed with the patient's blood several times per day.

In the case of another measurement system, currently available on the market, for measuring the glucose content, glucose is drawn through the skin by means of current pulses and collected in two gel discs of a sensor, which measures the glucose content. The sensor, which is disposed on the back of a watch-type display device, is a so-called minimally invasive system, i.e., a system with which it is necessary either to apply something to the skin or to insert small cannulae into the skin, as a result of which a risk of infection cannot be precluded. For this reason, in the case of this invasive system, it is necessary for the sensor to be changed every few days, in addition to which this system likewise requires calibration with the patient's blood. Both known systems mentioned are also termed Holter systems, i.e., systems to be applied by a doctor rather than by the patient themselves.

The object of the invention is to disclose a sensor system which is suitable for application by the patient and enables the latter continuously to monitor the glucose content of their blood, without the need for a repeated intervention just a short time after implantation of the sensor or for manipulations on or into the patient's skin which constitute a risk of infection.

The object set is achieved, according to the invention, in that the sensor is in the form of an ampoule which contains a sensitive liquid and into which glucose can penetrate, in that the viscosity of the mixture consisting of the sensitive liquid and the glucose is measured, and in that the user device consists of a portable device worn externally on the skin, the measurement and its evaluation being controlled through the user device.

In the case of the sensor system according to the invention, the user device does not effect any manipulation whatsoever on or into the skin, thus precluding any risk of irritation or infection. The sensor can be implanted for at least several months without the need for recalibration or suchlike, and the patient is spared the inconvenience of drawing blood. The patient can check the glucose content of his/her blood at any time, without discomfort of any kind, and regulate this glucose content by taking appropriate medicines without the need for supervision by a doctor.

A first preferred embodiment of the sensor system according to the invention is characterized in that the viscosity is measured on the basis of the oscillatory behaviour of an oscillating element which is disposed in the sensor and can be excited to oscillate by an oscillating magnetic field. The oscillatory behaviour of the oscillating element is analysed on the basis of its decay behaviour following switch-off of the magnet, the oscillating element itself generating a magnetic field which is measured by the user device.

A second preferred embodiment of the sensor system according to the invention is characterized in that the viscosity is measured on the basis of the rotation of a measuring element which is disposed in the sensor and which can be driven by a driving magnet likewise disposed in the sensor. The rotation of the measuring element is preferably analysed on the basis of its decay behaviour following switch-off of the driving magnet.

The sensor is preferably of a two-stage construction, and has a head portion and a measuring portion, the head portion containing the driving magnet and the measuring portion containing the measuring element, and the driving magnet being disposed in a casing, so as to be shielded against liquid.

A third preferred embodiment of the sensor system according to the invention is characterized in that provided between the head portion and the measuring portion is a reference portion, joining the latter two portions, which comprises a chamber that is sealed against liquid and includes a rotatably mounted reference element and the said sensitive liquid. The reference portion increases the accuracy of the measurement and reduces the effects of temperature changes on the measurement result.

The invention is explained more fully in the following with reference to an exemplary embodiment and the drawings, wherein:

FIGS. 1, 2 each show a perspective representation of a first exemplary embodiment of the partially open sensor of a sensor system according to the invention, FIG. 3 shows a cross section through the sensor of FIGS. 1, 2;

Figure 1:
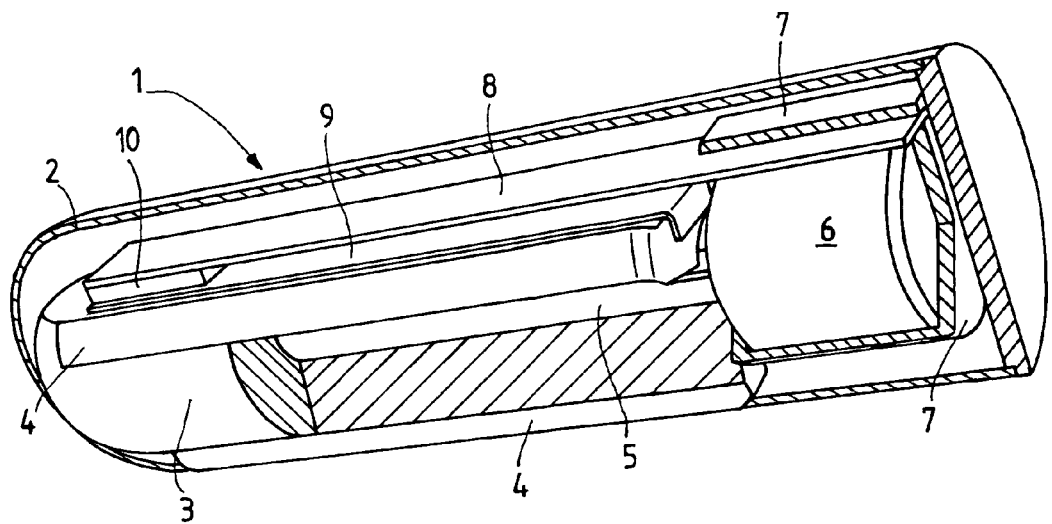
Figure 2:
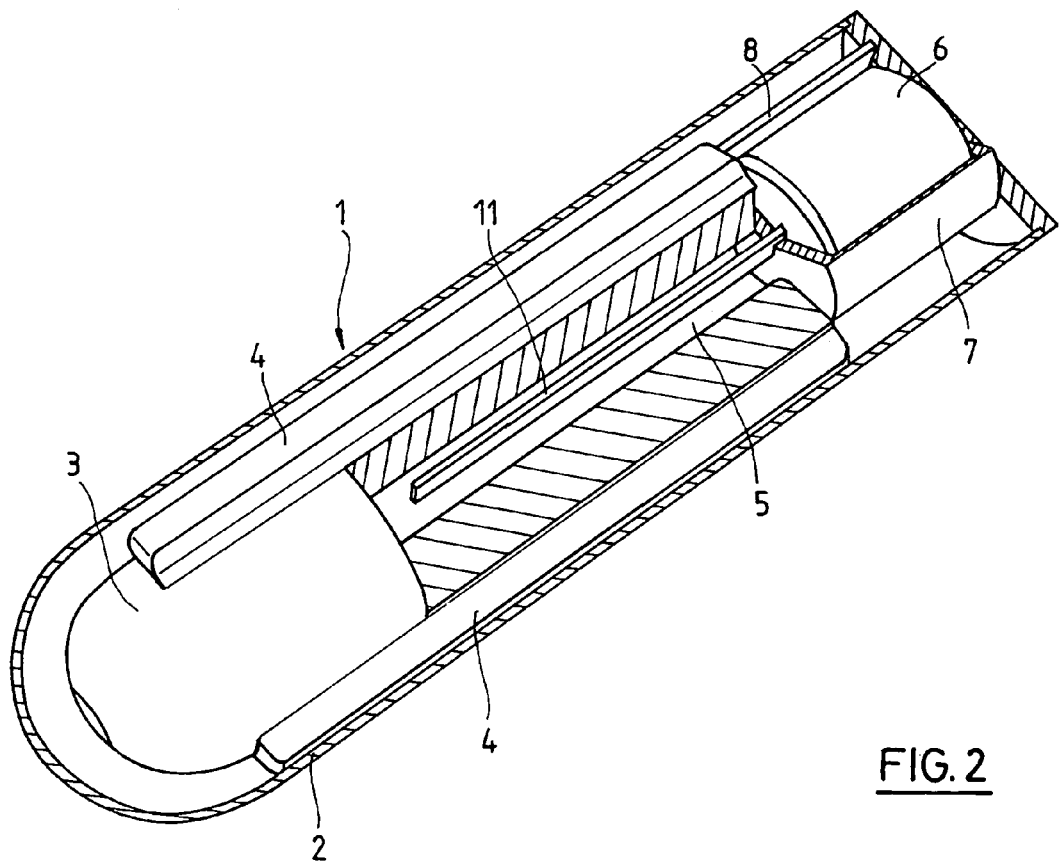
Figure 3:
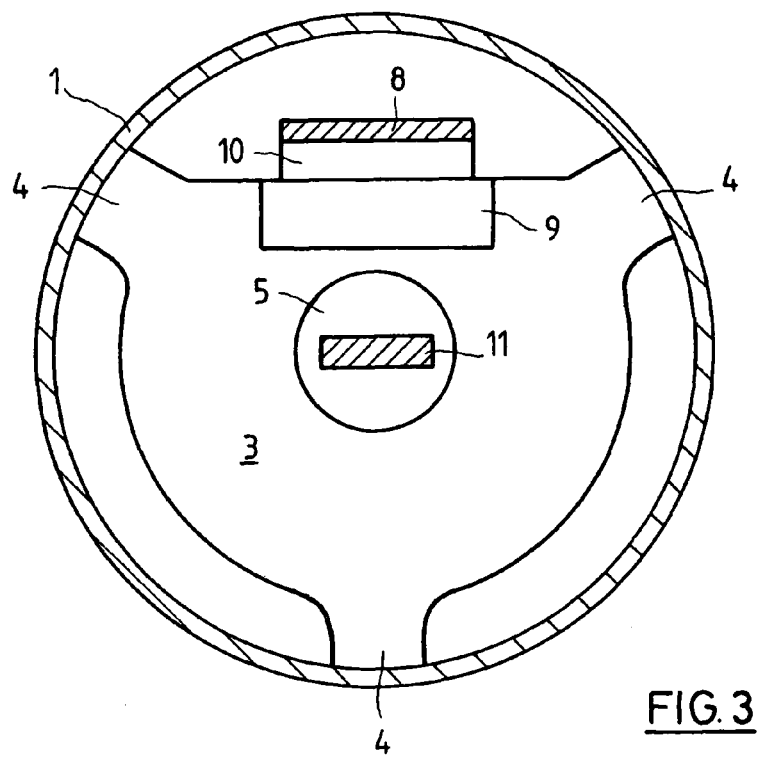

The first exemplary embodiment of the sensor 1, represented in FIGS. 1 to 3, has the form of an elongated ampoule having the approximate dimensions of 2 mm in diameter and 8 mm in length, these values being variable within wide limits. The shell 2 of the sensor 1 consists of a semipermeable wall, composed of cellulose, through which glucose can penetrate into the ampoule. The majority of the interior of the sensor 1 is taken up by a cylindrical plastic part 3, which is centred in the sensor 1 by several ribs 4 projecting on its circumferential surface and has an axial bore 5. The plastic part, which is, for example, an injection-moulded part produced from polycarbonate, serves both to support an oscillating element, described more fully below, and to reduce the liquid volume in the sensor 1. When ready for operation, the sensor is filled with a sensitive liquid having a high molecular weight, for example, Dextran and ConA.

Disposed in the sensor 1, adjoining that which, in FIGS. 1 and 2, is the right-hand end of the plastic part 3, is a permanent magnet 6, which is oversprayed with a plastic coating 7 of polycarbonate in order to prevent corrosion. In FIGS. 1 and 2, the plastic coating 7, the shell 2 of the sensor 1 and the plastic part 3 are partially open, in order to provide a view of the interior of the plastic part 3. The plastic coating 7 serves to support a bending bar 8 composed of, for example, aluminium oxide ceramic, which extends along the plastic part 3. The plastic part 3 is flattened (FIG. 3) in the region of the bending bar 8, having in this location a base substrate 9 in the form of a thin strip. Provided between the free end of the bending bar 8 and the base substrate 9 is a spacer 10, the thickness of which is selected so as to permit a sufficiently large oscillation amplitude of the bending bar, of about 100 μm.

The bending bar 8, base substrate 9 and spacer 10 are composed of the same material, and are produced by superimposing layers of laminates and subsequent packing. On its end face which faces towards the plastic part 3, the plastic coating 7 supports a narrow, elongated arm 11, which projects into the bore 5 of the plastic part 3. When the permanent magnet 6 is excited by an external oscillating magnetic field, it vibrates and, with the vibration of the magnet 6, the plastic coating 7, the bending bar 8 and the arm 11 also vibrate. These vibrations result in the sensitive liquid present in the sensor 1 being mixed with the glucose which has entered the sensor 1. The vibration of the arm 11 in this case is very important for a rapid measurement, since it simulates the flow in the sensor 1 and provides for a homogeneous glucose concentration in the sensor.

The frequency of the magnetic field exciting the magnet 6 is selected so that the latter vibrates at a frequency in the range of between 100 and 300 Hz. The bending bar 8 and arm 11 vibrate at the same frequency, the oscillation amplitude being about 100 μm or 0.1 mm. Following the mixing together of sensitive liquid and glucose, the magnetic field is switched off and the vibration decay time is measured, this being effected by means of the magnetic field generated by the magnet 6 oscillating together with the bending bar 8.

The change in viscosity of Dextran and ConA in a physiologically saline solution, as a function of the glucose concentration, is described in R. Ehwald et al., "Viscosimetric affinity assay", Anal Biochem 234, 1 (1996) and U. Beyer, "Recording of subcutaneous glucose dynamics by a viscosimetric affinity sensor", Diabetologia 44, 416 (2001). The solution described therein is based on the circulation of the sensitive liquid through a system consisting of several components. In the case of the system according to the invention, the viscosity is measured directly in the volume of the sensitive liquid enclosed in the sensor 1, the sensor being implanted under the skin, perpendicularly relative to the body surface in the longitudinal direction, so that the end of the sensor 1 which is the flat, right-hand end in FIGS. 1 and 2 lies about 2 mm below the skin. The implantation is effected at, for example, waist level, by means of an injection needle.

Figure 4:
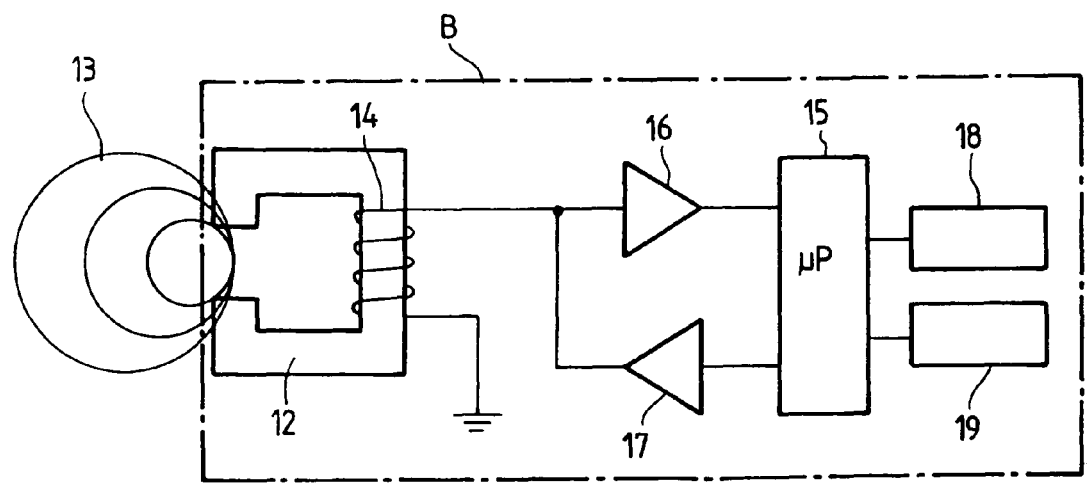
FIG. 4 shows a block diagram of the user device of the sensor system according to the invention.

FIG. 4 shows a block diagram of the user device denoted by the reference B. This device includes, in particular, a magnet 12 for generating a magnetic field 13 for excitation of the magnet 6 in the ampoule 1 (FIG. 1) and a coil 14 for excitation of the magnet 12, these simultaneously serving as a magnetic-field sensor for detecting the magnetic field generated by the magnet 6 in the sensor 1, and a microprocessor 15. The coil 14 is connected both to a receiving amplifier 16 and to a transmitting amplifier 17, the respective output and input of which are routed to the microprocessor 15. The microprocessor 15 is additionally connected to a display 18 for the currently measured glucose value and to a memory 19 for storing the glucose values. The user device B also includes an electric power supply, not represented. An additional magnetic-field sensor, for example a Hall sensor, may optionally be provided for precise positioning (normalization) of the user device B relative to the sensor 1.

Another possible solution for the excitation and detection functions of the user device B is based on a rotating dipole, the oscillations of the bending bar 8 being externally excited by a hard-disk motor having two permanent magnets, and the performance factor of the oscillator (bending beam 8 plus magnet 6) being determined through analysis of the motor attenuation.

Figure 5:
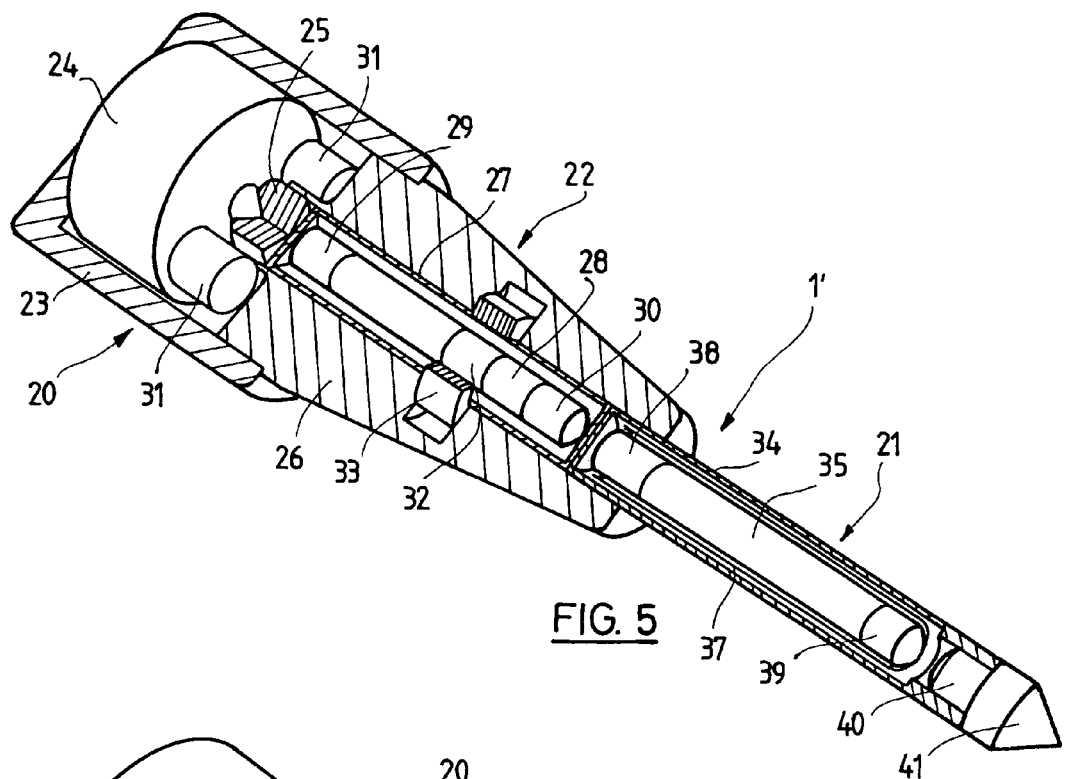
FIG. 5 shows a perspective representation of a second exemplary embodiment of the partially open sensor of a sensor system according to the invention.
Figure 6:
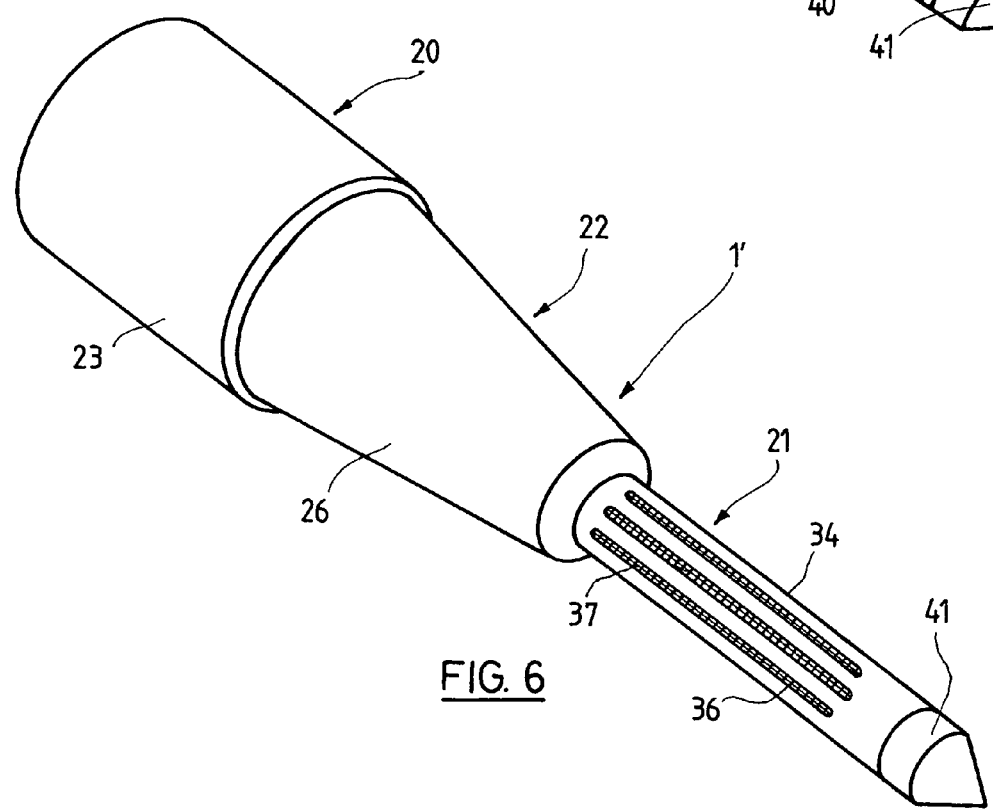
FIG. 6 shows a perspective view of the sensor of FIG. 5, in the closed state.

The sensor 1' represented in FIGS. 5 and 6 likewise has the form of an elongated ampoule; it differs, substantially, from the sensor 1 represented in FIGS. 1 to 3 in the method of measuring the viscosity of the mixture consisting of the sensitive liquid and the glucose. Whereas, in the case of sensor 1, the viscosity is measured on the basis of the oscillatory behaviour of an oscillating element, in the case of the second sensor 1' it is measured on the basis of the rotational behaviour of a measuring element. In this case it is sufficient, in principle, to analyse the rotational behaviour of the measuring element on the basis of its decay behaviour following switch-off of the magnet. The measurement result becomes more accurate, however, if two measuring elements are used, one rotating in the mixture consisting of sensitive liquid and glucose and the other rotating in a reference liquid. The reference liquid preferably consists of sensitive liquid.

According to FIGS. 5 and 6, the sensor 1' is rotationally symmetrical in form and consists of a cylindrical head portion 20, a cylindrical measuring portion 21, of a lesser diameter than the head portion 20, and a conical reference portion 22 joining the head portion 20 and the measuring portion 21. The head portion 20 has a diameter of approximately 2.5 mm and a length of approximately 3 mm, the measuring portion 21 has a diameter of approximately 0.6 mm and a length of approximately 6 mm, and the reference portion 22 likewise has a length of approximately 6 mm. The head portion 20 consists of an air-tight casing 23 in which is mounted a driving magnet 24. The driving magnet 24 is mechanically supported on two bearings 25, of which only the front bearing, mounted in the reference portion 22, is visible in FIG. 5. The rear bearing 25, concealed by the driving magnet 24, is mounted on the casing 23.

The reference portion 22 comprises a casing 26, in the form of a truncated cone, which has an axial bore in which is disposed an air-tight, cylindrical reference chamber 27. The casing 26 in the form of a truncated cone is joined, at its thicker end, to the head portion 20 and, at its thinner end, to the measuring portion 21. In the reference chamber 27 there is a reference liquid which preferably consists of the sensitive liquid, having a high molecular weight, mentioned in the description of FIGS. 1 to 3. Also in the reference chamber 27 is a rotatably mounted cylindrical reference element 28.

At each end, the reference element 28 carries a magnetic end portion 29 and 30, of which the end portion 29 forms a magnetic coupling with the driving magnet 24 and with two permanent magnets 31 projecting from the latter, and the end portion 30 forms a magnetic coupling with the measuring portion 21. Between the two magnetic end portions 29 and 30, the reference element 28 carries a further permanent magnet 32 which is located at the level of an annular magnet 33 which is disposed in the casing 26 and encompasses the reference chamber 27. The annular magnet 33 and permanent magnet 32 serve to stabilize the reference element 28 in its rotational axis. This stabilization can also be achieved through a mechanical positioning of the axis.

The measuring portion 21 comprises a cylindrical casing 34 which is attached, at one end, in the reference portion 22 and, at is other end, carries a closing portion 41. The casing 34 forms a measurement chamber which contains the said sensitive liquid and in which, in addition, a cylindrical measuring element 35 is rotatably mounted. The circumferential surface of the casing 34 is provided with longitudinal windows 36 and lined on the inside with a semipermeable membrane 37, composed of cellulose, through which glucose can penetrate into the measuring chamber. The rotation of the measuring element 35 causes the sensitive liquid present in the measuring chamber to be mixed with the glucose which has entered the latter, resulting in a homogeneous glucose concentration in the measuring chamber.

At its ends, the measuring element 35 carries a magnetic end portion 38 and 39 respectively, of which the end portion 38 adjacent to the reference element 28 effects a magnetic coupling with the reference element 28 and thus serves to drive the measuring element 35. The other end portion 39 forms a magnetic coupling with a permanent magnet 40, which is fixed at the free end of the casing 34, and serves to stabilize the measuring element 35 in its rotational axis. The reference 41 denotes a conical closing portion of the measuring portion 21 of the sensor.

The user device for the second exemplary embodiment of the sensor represented in FIGS. 5 and 6 is of substantially the same construction as the user device B represented in FIG. 4, differing from the latter mainly in that it contains several coils 14 for generating a rotating field which causes the driving magnet 24 to rotate. Analogously, the user device comprises several magnetic-field sensors, which measure the rotation of the driving magnet 24 following switch-off of the rotating magnetic field.

The driving magnet 24, via the magnets 31 and 29, drives the reference element 28, and the latter drives the measuring element 35 via the magnets 30 and 38. The measuring element 35 and the reference element 28 rotate in the casings 27 and 34, both of which contain the same sensitive liquid having a high molecular weight. The casing 27 having the reference element 28 is sealed in an air-tight manner and the casing 34 having the measuring element 35 is sealed with the semipermeable membrane 37, through which glucose can penetrate into the measuring chamber. The magnetic coupling between the reference element 28 (permanent magnet 30) and the measuring element 35 (permanent magnet 38) is of such design that the measuring element 35 effects coupled rotation only to a critical rotational frequency.

Above this critical frequency, the system measures the viscosity of the liquid in the casing 27 on the basis of the decay of the rotation of the driving magnet 24 upon switch-off of the rotating magnetic field, this liquid being exclusively the said sensitive liquid. Below the critical frequency, the decay of the rotation of the driving magnet 24 upon switch-off of the rotating magnetic field is determined by the viscosity of the liquid mixture, consisting of sensitive liquid and glucose, in the measuring chamber (casing 34). The glucose concentration determined on this basis of this information is non-dependent on the temperature, this constituting a substantial advantage over a system without reference measurement.

If this advantage is not required or not essential, the sensor represented in FIGS. 5 and 6 may be simplified by omission of the reference portion 22. In this case, the driving magnet would drive the measuring element 35 directly, via the permanent magnets 31 and 38.

The sensor 1 represented in FIGS. 1 to 3 may be adapted, through relatively simple modification, for application as a Holter system, in which the glucose content is continuously monitored under medical supervision over a period of several days. In the case of this application, the magnetic field exciting the magnet 6 in the sensor 1 is generated, not by an external magnet 12, but by a current coil disposed inside the sensor 1, two thin electric wires being passed outwards from the said current coil, through the skin of the patient, to the user device. The said current coil is preferably disposed in the region of the spacer 10 (FIG. 1). In order to assure a sufficient magnetic flux from the current coil to the magnet 6, the bending bar 8 and the base substrate 9 are composed of magnetically soft material. The same applies to the sensor 1' represented in FIGS. 5 and 6 in which, likewise, a current coil for excitation of the driving magnet 24 could be disposed inside the casing 23.

The invention claimed is:

1. Sensor system for determining a glucose concentration in blood, comprising an implantable sensor (1, 1') and a user device (B) associated with the latter, wherein the sensor (1, 1') is in the form of an ampoule which contains a sensitive liquid and into which glucose can penetrate, in that a viscosity of the mixture consisting of the sensitive liquid and the glucose is measured, and in that the user device (B) consists of a portable device configured to be worn externally on the skin, the measurement and its evaluation being controlled through the user device (B) and wherein the viscosity is measured on the basis of an oscillatory behaviour of an oscillating element (8) in the form of a bending bar which is disposed in the sensor (1) and can be excited to oscillate by an oscillating magnetic field, and wherein a plastic part (3) is disposed in the sensor (1), partially filling the latter and confining the liquid volume, and is designed as a support for the oscillating element (8) and has an elongated bore (5) into which there projects an arm (11) which is disposed on a magnet (6) and which is provided for mixing the liquids together.

2. Sensor system according to claim 1, wherein the oscillatory behaviour of the oscillating element (8) is analysed on the basis of its decay behaviour following switch-off of a magnet (6), the oscillating element (8) itself generating a magnetic field which is measured by the user device.

3. Sensor system according to claim 1, wherein the oscillating element additionally homogenizes the liquid in the sensor (1).

4. Sensor system according to claim 3, wherein the oscillating element (8) is positively joined to a magnet (6).

5. Sensor system according to claim 4, wherein the bending bar has two ends and the magnet (6) is attached to one of the two ends of the bending bar and can be caused to oscillate by a magnetic field (13).

6. Sensor system according to claim 5, wherein the said magnetic field (13) is generated by an electromagnetic arrangement provided in the user device (B) or by an electric coil provided in the sensor (1).

7. Sensor system according to claim 1, wherein the sensor (1) comprises a semi-permeable wall (2) which permits penetration by glucose.

8. Sensor system according to claim 6, wherein the said electromagnetic arrangement includes means for excitation of the magnet (6) in the sensor (1) and a magnetic-field sensor for the magnetic field generated by this magnet.

9. Sensor system according to claim 8, wherein the said means and the said magnetic-field sensor consist of a magnet (12) and a coil (14) exciting the latter, and of a microprocessor (15) connected to the coil (14).

10. Sensor system for determining a glucose concentration in blood, comprising an implantable sensor (1, 1') and a user device (B) associated with the latter, wherein the sensor (1, 1') is in the form of an ampoule which contains a sensitive liquid and into which glucose can penetrate, in that a viscosity of the mixture consisting of the sensitive liquid and the glucose is measured, and in that the user device (B) consists of a portable device configured to be worn externally on the skin, the measurement and its evaluation being controlled through the user device (B), wherein the viscosity is measured on the basis of a rotation of a measuring element (35) which is disposed in the sensor (1') and which can be driven by a driving magnet (24), the rotation of the measuring element (35) being analysed on the basis of its decay behaviour following switch-off of the driving magnet (24).

11. Sensor system according to claim 10, wherein the driving magnet (24) is disposed in the sensor.

12. Sensor system according to claim 11, wherein the sensor (1') is of a two-stage construction, and has a head portion (20) and a measuring portion (21), the head portion (20) containing the driving magnet (24) and the measuring portion (21) containing the measuring element (35), and the driving magnet (24) being disposed in a casing (23), so as to be shielded against liquid.

13. Sensor system according to claim 12, wherein provided between the head portion (20) and the measuring portion (21), is a reference portion (22), joining the latter two portions, which comprises a chamber (27) that is sealed against liquid and includes a rotatably mounted reference element (28) and the said sensitive liquid.

14. Sensor system according to claim 12, wherein the head portion (20) and the measuring portion (21) are each of a cylindrical form, the diameter of the head portion (20) being greater than that of the measuring portion (21).

15. Sensor system according to claim 13, wherein the reference portion (22) has the form of a truncated cone, and in that the reference element (28) and the measuring element (35) are designed as elongated cylinders.

16. Sensor system according to claim 15, wherein the measuring portion (21) is designed as an elongated casing (34) which comprises window-type openings (36) and is lined on the inside with a semi-permeable film (37) which permits penetration by glucose.

17. Sensor system according to claim 16, wherein the driving magnet (24) can be caused to rotate by a magnetic field which is generated by an electromagnetic arrangement provided in the user device (B).

18. Sensor system according to claim 17, wherein the measuring element (35) is driven via magnetic couplings (29, 31; 30, 38) between the driving magnet (24) and the reference element (28) and between the reference element (28) and the measuring element (35), respectively.

19. Sensor system according to claim 18, wherein the magnetic coupling (30, 38) between the reference element (28) and the measuring element (35) is of such design that the measuring element (35) effects coupled rotation only to a certain critical rotational frequency.

20. Sensor system according to claim 19, wherein, following switch-off of the drive of the driving magnet (24), a decay of its rotation is determined, above a critical rotational frequency, exclusively by the viscosity of the sensitive liquid in the chamber (27) of the reference portion (22) and, below the critical rotational frequency, by the viscosity of the mixture consisting of sensitive liquid and glucose in the casing (34) of the measuring portion (21).

21. Sensor system according to claim 20, wherein a value of the glucose concentration, which is non-dependent on the temperature, is determined on the basis of the two viscosity values above and below the critical rotational frequency.

* * * * *